United States Patent [19]

Atwal

[11] Patent Number: 5,393,771
[45] Date of Patent: Feb. 28, 1995

[54] 4-SUBSTITUTED BENZOPYRAN AND RELATED COMPOUNDS

[75] Inventor: Karnail S. Atwal, Newtown, Pa.

[73] Assignee: Brisol-Myers Squibb Company, Princeton, N.J.

[21] Appl. No.: 60,848

[22] Filed: May 12, 1993

[51] Int. Cl.$^6$ .................. A61K 31/35; C07D 311/68; C07D 405/04; C07D 405/12

[52] U.S. Cl. .................. 514/394; 514/457; 548/305.1; 549/404

[58] Field of Search ............... 548/305.1; 514/394, 514/457; 549/404

[56] References Cited

U.S. PATENT DOCUMENTS

| | | | |
|---|---|---|---|
| 3,933,847 | 1/1976 | Ohkawa et al. | 548/305.1 |
| 4,238,501 | 12/1980 | Kabbe et al. | 514/456 |
| 4,575,511 | 3/1986 | Evans et al. | 548/305.1 |
| 4,764,622 | 8/1988 | Claussen et al. | 548/305.1 |
| 4,988,723 | 1/1991 | Shiokawa et al. | 548/305.1 |
| 5,028,711 | 3/1986 | Stenzel et al. . | |
| 5,082,858 | 1/1992 | Garcia et al. | 549/404 |
| 5,096,914 | 3/1992 | Stenzel et al. . | |
| 5,140,031 | 8/1992 | Atwal et al. | 514/394 |

FOREIGN PATENT DOCUMENTS

| | | | |
|---|---|---|---|
| 168619 | 1/1986 | European Pat. Off. | 514/302 |
| 205292 | 12/1986 | European Pat. Off. | 514/302 |
| 214818 | 3/1987 | European Pat. Off. | 514/302 |
| 274821 | 7/1988 | European Pat. Off. | 514/302 |
| 322251 | 6/1989 | European Pat. Off. | 514/302 |
| 344747 | 12/1989 | European Pat. Off. | 514/302 |
| 359537 | 3/1990 | European Pat. Off. | 514/302 |
| 389861 | 10/1990 | European Pat. Off. | 514/302 |
| 412531 | 2/1991 | European Pat. Off. | 514/302 |
| 0462761 | 12/1991 | European Pat. Off. . | |
| 8500602 | 2/1985 | WIPO | 514/302 |
| 8707607 | 12/1987 | WIPO | 514/302 |

OTHER PUBLICATIONS

H. J. Petersen et al., "Synthesis and Hypotensive Activity of N-Alkyl-N'''-cyano-N'-pyridylguanidines", *J. of Med. Chem.*, vol. 21, No. 8, (Aug. 1978), pp. 773–781.

V. A. Ashwood et al., "Synethsis and Antihypertensive Activity of 4-(Cyclic amido)-2H-1-benzopyrans", *J. Med. Chem.*, (1986), 29, 2194–2201.

C. R. Rasmussen et al., "Improved Procedures for the Preparation of Cycloalkyl-, Arylalkyl-, and Arylthioureas", *Synthesis*, (Jun. 1988), pp. 456–459.

V. V. Mozolis et al., "Preparation of N-Substituted Thiourea", *Russian Chem. Reviews*, 42(7), (1973), pp. 587–595.

J. M. Evans et al., "Synthesis and Antihypertensive Activity of Substituted trans-4-Amino-3,4-dihydro-2,-2-dimethyl-2H-1-benzopyran-3-ols", *J. Med. Chem.*, (1983), 26, pp. 1582–1589.

R. W. Lang et al., "Synthesis of Selectively Trifluoromethylated Pyridine Derivatives as Potential Antihypertensives", *Helvetica Chimica Acta*, (1988), vol. 71, pp. 596–601.

(List continued on next page.)

*Primary Examiner*—Floyd D. Higel
*Attorney, Agent, or Firm*—Ellen K. Park

[57] ABSTRACT

Compounds having the formula

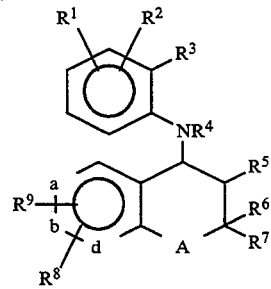

and pharmaceutically acceptable salts thereof. These compounds have potassium channel activating activity and are useful, therefore for example, as cardiovascular agents.

4 Claims, No Drawings

OTHER PUBLICATIONS

P. Sebok et al., "Selective syknthesis of Analogues of the Natural Precocenes, Synthesis and Regioselective (-Alkylation of 6-Chloro- and 6-Tert-Butyl-7,-8-Dihyedroxy-2,2-Dimethyl-4-Chromanones", *Heterocycles*, (1988), 27, pp. 2595-2607.

P. Teixidor et al., "Improved Preparation of Precocene II, Unexpected Results in the Reduction of Alkoxy Substituted Acetophenones and 4-Chromanones with Sodium Borohydride", *Heterocycles*, (1988), 27, pp. 2459-2465.

A. Banerji et al., "Enolates of o-Hydroxyacetophenones: Novel Syknthesis of 2,2-Dialkyl-4-Chromanones", *Tetrahedron Letters*, No. 38, 1979, pp. 3685-3686.

G. Ariamala et al., "A Simple Route for the Synthesis of 4-Chlorochromenes and Chroman-4-ones", *Tetrahydron Letters*, (1988), vol. 29, No. 28, pp. 3487-3488.

4-SUBSTITUTED BENZOPYRAN AND RELATED COMPOUNDS

BRIEF DESCRIPTION OF THE INVENTION

The present invention is directed to compounds of the formula

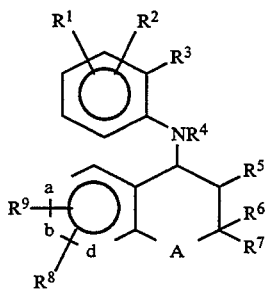

and pharmaceutically acceptable salts thereof. As used in formula I, and throughout the specification, the symbols have the following meanings:

a, b and d are all carbon atoms or one of a, b and d is a nitrogen atom or —N(O)— and the others are carbon atoms;

A is a single bond, —$CH_2$—, —O—, —S— or —N(R)— where R is hydrogen, alkyl, haloalkyl, aryl, arylalkyl, cycloalkyl or (cycloalkyl)alkyl;

$R^1$ is hydrogen, alkyl, halo, haloalkyl, nitro or cyano;

$R^2$ is hydrogen, alkyl or halo;

$R^3$ is —COR, —CO-amino, —CO-substituted amino, —NRCOOR*, —NRCO-amino or —NRCO-substituted amino (where R* is the same or different R, as defined above);

$R^4$ is hydrogen, alkyl, alkenyl, aryl, arylalkyl, cycloalkyl or (cycloalkyl)alkyl; or $R^3$ and $R^4$ together with the carbon and nitrogen atoms to which they are attached, form a fused imidazole ting, optionally substituted at an available carbon atom of the imidazole portion with one or more substituents selected from hydrogen, alkyl, cyano, —COR, —COOR, —CO-amino, —CO-substituted amino, —NRCOOR*, —NRCO-amino or —NRCO—substituted amino;

$R^5$ is hydrogen, hydroxy or —OC(O)R (R as defined above);

$R^6$ and $R^7$ are each independently hydrogen, alkyl or arylalkyl, or $R^6$ and $R^7$ taken together with the carbon atom to which they are attached form a 5- to 7-membered carbocyclic ring;

$R^8$ is hydrogen, alkyl, haloalkyl, alkenyl, alkynyl, cycloalkyl, arylalkyl, (cycloalkyl)alkyl, —CN, —$NO_2$, —COR, —COOR, —CONHR, —$CONR^5$, —$CF_3$, S-alkyl, —SOalkyl, —$SO_2$alkyl,

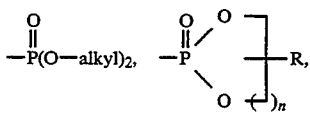

halogen, amino, substituted amino, —O-alkyl, —$OCF_3$, —$OCH_2CF_3$, —OCOalkyl, —OCONRalkyl, —NRCOalkyl, —NRCOOalkyl or —$NRCONR^5$;

$R^9$ is hydrogen, alkyl, hydroxy, —O-alkyl, amino, substituted amino, —NHCOR, —CN or —$NO_2$; and n is an integer of 1 to 3, provided that when a, b and d are carbon atoms, $R^3$ is —NRCOOR* and $R^4$ is hydrogen, that one of $R^1$ or $R^2$ is other than hydrogen.

These compounds possess antiischemic activity and are useful, for example as cardiovascular agents.

DESCRIPTION OF THE INVENTION

The present invention provides for compounds of formula I, pharmaceutical compositions employing such compounds and for methods of using such compounds. Listed below are definitions of various terms used to describe the compounds of the instant invention. These definitions apply to the terms as they axe used throughout the specification (unless they are otherwise limited in specific instances either individually or as part of a larger group.

The term "alkyl" refers to both straight and branched chain groups having 1 to 8 carbon atoms in the normal chain, preferably 1 to 5 carbons, such as methyl, ethyl, propyl, butyl, pentyl, hexyl, heptyl, octyl, the various branched chain isomers thereof, such as isopropyl, t-butyl, isobutyl, isohexyl, 4,4-dimethylpentyl, 2,2,4-trimethylpentyl and the like as well as such groups including a halo substituent, such as f, Br, Cl or I such as $CCl_3$ or $CF_3$, an alkoxy substituent, an aryl substituent, an alkylaryl substituent, a haloaryl substituent, a cycloalkyl substituent, a (cycloalkyl)alkyl substituent, a hydroxy substituent, an alkylamino substituent, an alkanoylamino substituent, an arylcarbonylamino substituent, a nitro substituent, a cyano substituent, a thiol substituent or an alkylthio substituent.

The term "alkoxy" refers to any of the above alkyl groups linked to an oxygen atom.

The term "alkylthio" refers to any of the above alkyl groups linked to a sulfur atom.

The term "alkenyl" refers to any of the above alkyl groups further containing at least one carbon to carbon double bond.

The term "alkynyl" refers to any of the above alkyl groups further containing at least one carbon to carbon triple bond.

The term "cycloalkyl" refers to saturated cyclic hydrocarbon groups containing 3 to 7 ring carbons with cyclopropyl, cyclopentyl and cyclohexyl being preferred.

The term "halogen" or "halo" refers to chlorine, bromine, iodine and fluorine.

The term "aryl" refers to phenyl, 1-naphthyl, 2-naphthyl; phenyl, 1-naphthyl, 2-naphthyl, mono-substituted with ($C_1$-$C_4$)-alkyl, ($C_1$-$C_4$)-alkylthio, ($C_1$-$C_4$)-alkoxy, halo, nitro, cyano, hydroxy, amino, —NH—($C_1$-$C_4$)-alkyl, —N(($C_1$-$C_4$)-alkyl), —$CF_3$, —$OCHF_2$,

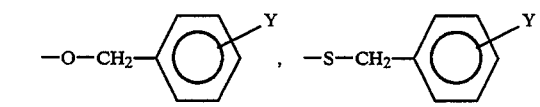

(wherein Y is hydrogen, ($C_1$-$C_4$)-alkyl, ($C_1$-$C_4$)-alkylthio, ($C_1$-$C_4$)-alkoxy, halo, hydroxy or —$CF_3$), —O—$CH_2$-cycloalkyl, or —S—$CH_2$-cycloalkyl; and phenyl, 1-naphthyl or 2-naphthyl, di-substituted with methyl, methoxy, methylthio, halo, —$CF_3$, nitro, amino or —$OCHF_2$. Preferred aryl groups include unsubstituted phenyl and monosubstituted phenyl wherein the substituents are (C₁-C₄)-alkyl, methoxy, halo, nitro, cyano or —CF₃.

The term "heterocyclo" or "hetero" refers to fully saturated or unsaturated rings of 5 or 6 atoms containing one or two oxygen and sulphur atoms and/or one to four nitrogen atoms provided that the total number of hetero atoms in the ring is four or less. The hetero ring is attached by way of an available atom. Preferred monocyclic hetero groups include 2- and 3-thienyl, 2- and 3-furyl, 2-, 3- and 4-pyridyl and imidazolyl. The term hetero also includes bicyclic rings wherein the five or six membered ring containing oxygen, sulphur and nitrogen atoms as defined above is fused to a benzene ring and the bicyclic ring is attached by way of an available carbon atom. Preferred bicyclic hetero groups include 4-, 5-, 6- or 7-indolyl, 4-, 5-, 6- or 7-isoindolyl, 5-, 6-, 7- or 8-quinolinyl, 5-, 6-, 7-or 8-isoquinolinyl, 4-, 5-, 6- or 7-benzothiazolyl, 4-, 5-, 6- or 7-benzoxazolyl, 4-, 5-, 6- or 7-benzimidazolyl, 4-, 5-, 6- or 7-benzoxadiazolyl and 4-, 5-, 6- or 7-benzofuranzanyl.

The term heterocyclo also includes such monocyclic and bicyclic rings wherein an available carbon atom is substituted with a (C₁-C₄)-alkyl, (C₁-C₄)-alkylthio, (C₁-C₄)-alkoxy, halo, nitro, keto, cyano, hydroxy, amino, —NH—(C₁-C₄)-alkyl, —N((C₁-C₄)-alkyl)2, —CF₃ or —OCHF₂ or such monocyclic and bicyclic rings wherein two or three available carbons have substituents selected from methyl, methoxy, methylthio, halo, —CF₃, nitro, hydroxy, amino and —OCHF₂.

The term "substituted amino" refers to a group of the formula —NZ₁Z₂ wherein Z₁ is hydrogen, alkyl, cycloalkyl, aryl, arylalkyl, (cycloalkyl)alkyl and Z₂ is alkyl, cycloalkyl, aryl, arylalkyl, (cycloalkyl)alkyl or Z₁ and Z₂ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl- 1-piperazinyl, 4-diarylalkyl- 1-piperazinyl, 1-pyrrolidinyl, 1-piperidinyl, or 1-azepinyl, substituted with alkyl, alkoxy, alkylthio, halo, trifluoromethyl or hydroxy.

The compounds of formula I can be present as salts, in particular pharmaceutically acceptable salts. If the compounds of formula I have, for example, at least one basic center, they can form acid addition salts. These are formed, for example, with strong inorganic acids, such as mineral acids for example surfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid, or such as benzoic acid, or with organic sulfonic acids, such as (C₁-C₄)-alkyl- or aryl-suffonic acids which are unsubstituted or substituted, for example by halogen, for example methane- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in diastereomeric forms or in mixtures thereof. The above described processes can utilize racemates, enantiomers or diastereomers as starting materials. When diastereomeric products are prepared, they can be separated by conventional methods for example, chromatographic or fractional crystallization. Preferred compounds are those with the 3S or 4R stereochemistry.

It should be understood that the present invention includes prodrug forms of the compounds of formula I such as alkylesters of acids.

The compounds of the instant invention may, for example, be in the free or hydrate form, and may be obtained by methods exemplified by the following descriptions.

Compounds of formula I where R³ is CO-amino or CO-substituted amino and R 1 and R² are hydrogens, may be prepared by coupling an amine of formula

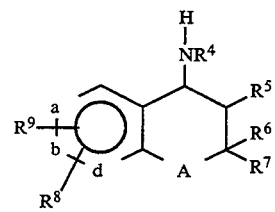

II with a compound of the formula

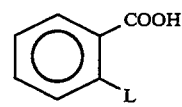

III where L is a leaving group such as chloro, iodo or bromo, in the presence of a copper salt such as copper acetate in an organic solvent such as hot dimethylformamide to form a compound of formula

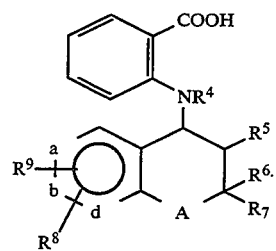

IV

Compounds of formula IV are then converted to compounds of formula I wherein $R^3$ is CO-amino or CO-substituted amino, and $R^1$ and $R^2$ are hydrogens under standard conditions which may then be used to form compounds of the formula I wherein $R^3$ is COR and $R^1$ and $R^2$ are hydrogens (using standard methodology).

Compounds of formula I wherein R3 is NHCOOR, NHCO-amino or NHCO-substituted amino can be prepared by first coupling a compound of formula II with a compound of formula

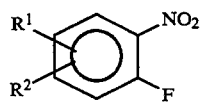  V to provide a compound of formula

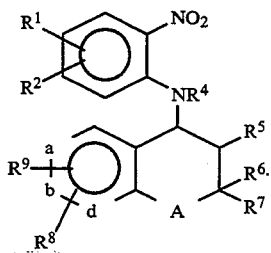  VI

The nitro group in formula VI is reduced with a reducing agent such as tin/hydrochloric acid or stannous chloride to provide a compound of formula

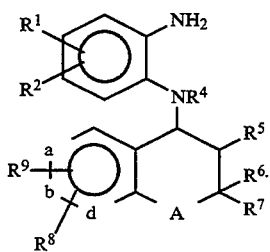  VII

The primary amine in compounds of formula VII can then be converted to compounds of formula I wherein $R^3$ is NHCOOR, NHCO-amino or NHCO-substituted amino by standard acylation methodology.

Compounds of formula I wherein $R^3$ is NHCOOR and $R^5$ is trans-hydroxyl, can also be prepared by treatment of an epoxide of formula VIII

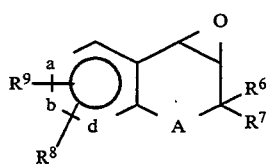  VIII with a compound of formula

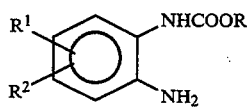  IX in the presence of a catalyst such as magnesium perchlorate in an organic solvent such as acetonitrile.

Compounds of formula I where $R^3$ is NRCOOR*, NRCO-amino or NRCO-substituted amino, where R is other than hydrogen, may be prepared by modification of the above described procedures using standard methodology such as alkylation.

Compounds of formula I wherein $R^3$ and $R^4$ together form a fused imidazole ring and $R^5$ is hydrogen, can be prepared by treatment of a compound of formula

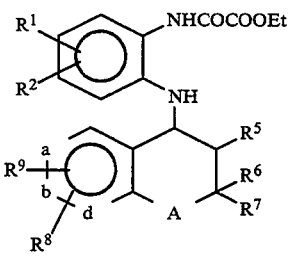  X with a chlorinating agent such as phosphorous oxychloride.

Compounds of formula I wherein $R^5$ is —OC(O)R (R as defined above) can be prepared from compounds of formula I wherein $R^5$ is hydroxyl by treatment with an acid chloride of formula ClCOR in the presence of a base such as pyridine or triethylamine.

The amine of formula II, where $R^5$ is hydrogen, can be prepared from a ketone of the formula

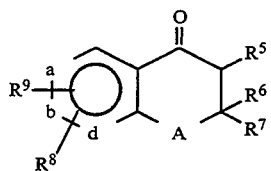  XI by standard methodology.

The amine of formula II wherein $R^5$ is hydrogen, can also be prepared from the olefin of the formula

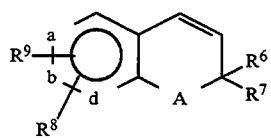  XII by a sequence of steps which involve: (a) camlyric hydrogenation of the double bond; (b) bromination of the resulting compound with N-bromosuccinimide and light; (c) displacement of the bromide with azide using sodium azide followed by; (d) catalytic reduction of the azide.

Compounds of formula H where $R^5$ is trans-hydroxy can be prepared by methods described in the literature, such as by J. M. Evans, et al., *J. Med. Chem.*, 26, 1582 (1983), J. M. Evans, et at., *J. Med. Chem.*, 29, 2194

(1986), R. W. Lang et al., *Helvetica Chimica Acta*, 71, 596 (1988), European patent 0205292 A2 and PCT patent 87/07607.

Compounds of formula II wherein $R^5$ is cis-hydroxy can be prepared by methods described by G. Burrell, et al., *Tetrahedron Letters*, 31, 3649 (1990).

Amines of formula II wherein A is a single bond can be prepared according to D. R. Buckle, et al., *J. Med. Chem.*, 34, 919 (1991).

Amines of formula II wherein A is $CH_2$ can be prepared by methods described in V. A. Ashwood, et al., *J. Med. Chem.*, 34, 3261 (1991).

To prepare the individual enantiomers of formula I, the enantiomers of the amines of formula II can be prepared and used in the above described reactions.

To prepare enantiomers of amine II wherein $R^5$ is trans-hydroxy and A is oxygen, the olefin of formula XII is epoxidized with an oxidizing agent such as commercial bleach using a metal catalyst such as chiral manganese catalyst of the formula

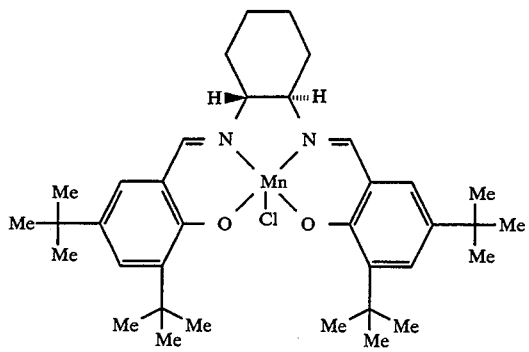

XIII as described by N. H. Lee, et at. (*Tetrahedron Letters*, 32, 5055-5058 (1991)), to provide predominantly the chiral epoxide of formula

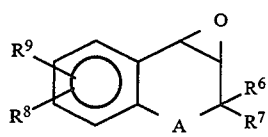

XIV or

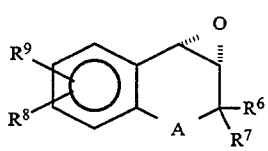

XV depending on the chirality of the 1,2-diaminocyclohexane used in formula XIII.

The epoxides of formulae XIV and XV can be reacted with an amine of formula $R^4NH_2$ to provide enantiomers of amine II wherein A is oxygen and $R^5$ is trans-hydroxyl.

The enantiomers of the compounds of formula I, may also be prepared from the amine of formula II wherein $R^5$ is hydrogen or hydroxyl by conversion to the diastereomeric amides of formulae

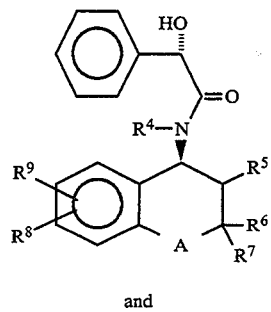

XVI and

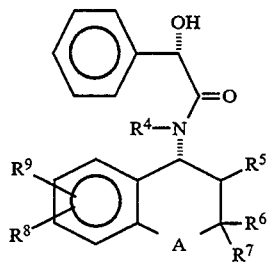

XVII by treatment with a chiral acid such as chiral non-racemic mandelic acid in the presence of a carbodiimide such as dicyclohexylcarbodiimide. The enantiomer of mandelic acid that yields crystalline amide with the desired stereochemistry is preferred in the resolution step.

Compounds of formula XVI and XVII may be separated by crystallization or chromatography as known in the art.

Compounds XVI and XVII are then hydrolyzed by heating in a high boiling polar solvent such as dioxane in the presence of a strong acid such as sulfuric acid to give enantiomers of the amine of formula II having the formulae

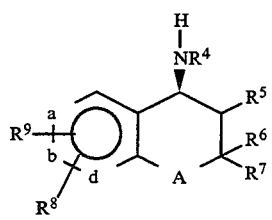

XVIII and

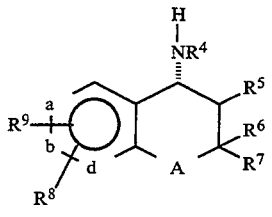

XIX wherein $R^5$ is hydrogen or hydroxyl.

Compounds of formula HI and V are commercially available or can be made by literature methods.

Compounds of formula VIII can be prepared by methods described in the literature, such as by J. M. Evans, et al., *J. Med. Chem.*, 26, 1582 (1983), J. M. Evans, et al., *J. Med. Chem.*, 29, 2194 (1986), R. W.

Lang et al., Helvetica Chimica Acta, 71, 596 (1988), European patent 0205292 A2 and PCT patent 87/07607.

Compounds of formula IX are readily prepared from commercially available substituted-2-nitro-anilines by first acylating the amine with a chloroformate of formula ClCOOR in the presence of a base such as pyridine and then reducing the nitro group with hydrogen gas using a catalyst such as palladium over charcoal.

Compounds of formula X can be prepared from compounds of formula VII wherein $R^5$ is hydrogen, by treatment with a oxalic acid derivative such as ethyloxalylchloride.

The ketone of formula XI can be obtained by literature methods as disclosed in P. Sebok et al., Heterocycles, 27, 2595 (1988), P. Teixidor et al., Heterocycles, 27, 2459 (1988), A. Benerji et al., Tetrahedron Letters, 3685 (1979) and G. Adamala et al., Tetrahedron Letters, 29, 3487 (1988).

Compounds of formula XII are obtained by literature methods described for the preparation of compounds of formula II and VIII.

The compounds of the present invention can have asymmetric centers at carbons 2–4 of the bicyclic ring. Also, any one of the R's can have an asymmetric carbon. Consequently, compounds of formula I can exist in diastereomeric forms or in mixtures thereof. The above described process can utilize racemates, enantiomers or diastereomers as starting materials. When diastereomeric products are prepared, they can be separated by conventional chromatographic or fractional crystallization methods.

The preferred compounds of the present invention are those compounds of formula I where:

a, b and d are carbon atoms;
A is —O—;
$R^1$ and $R^2$ are hydrogens;
$R^3$ and $R^4$ together with the carbon and nitrogen atoms to which they are attached form a fused imidazole ring;
$R^5$ is hydrogen or hydroxy; and
$R^6$ and $R^7$ are alkyl.

Compounds of formula I may be used as antiischemic agents, i.e., for the treatment of ischemic conditions such as myocardial ischemia, cerebral ischemia, lower limb ischemia and the like.

Thus a composition containing one (or a combination) of the compounds of this invention, may be administered to a species of mammal (e.g., humans) suffering from an ischemic or hypertensive condition.

A single dose, or two to four divided daily doses, provided on a basis of about 0.001 to about 100 mg per kilogram of body weight per day, preferably about 0.1 to about 25 mg per kilogram of body weight per day is appropriate. The substance is preferably administered orally, but parenteral routes such as the subcutaneous, intramuscular, intravenous or intraperitoneal routes or any other suitable delivery system, such as intranasal or transdennal routes can also be employed.

As a result of the potassium channel activating activity of compounds of this invention, these compounds are also useful in the treatment of cardiovascular disorders and any disorders associated with smooth muscle contraction. For example, compounds of the present invention are useful as therapy for congestive heart failure, therapy for peripheral vascular disorders (e.g. Raynaud's Disease), therapy for pulmonary hypertension, as anti-anginal agents, as antifibrillatory agents, as thrombolytic agents and in limiting myocardial infarction.

Compounds of the present invention are additionally expected to be useful in the treatment of central nervous system disorders (e.g., Parkinsonism, as anti-tremor agents, epilepsy), in therapy for renal failure, in therapy for urinary incontinence, as anti-diarrheal agents, in therapy for pre-eclampsia, dysmenorrhea and premature labor, as well as for the promotion of hair growth (e.g., in the treatment of male pattern baldness) and as anti-asthmatic agents.

The compounds of this invention can also be formulated in combination with a diuretic such as chlorothiazide, hydrochlorothiazide, flumethiazide, hydroflumethiazide, bendroflumethiazide, methylchlothiazide, trichloromethiazide, polythiazide or benzthiazide as well as ethacrynic acid tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or calcium channel blocking agents such as nifedipine or diltiazem. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to about 500 milligrams of a compound of formula I is compounded with physiologically acceptable vehicle, carder, excipient, binder, preservative, stabilizer, flavor, etc., in a unit dosage form as called for by accepted pharmaceutical practice. The amount of active substance in these compositions or preparations is such that a suitable dosage in the rang indicated is obtained.

The following examples and preparations describe the manner and process of making and using the invention and are illustrative rather than limiting. It should be understood that there may be other embodiments which fall within the spirit and scope of the invention as defined by the claims appended hereto.

EXAMPLE 1 trans-[2-[(6-Cyano-3,4-dihydro-3-hydroxy-2,2-dimethyl- 2H-pyran-4yl)amino]-phenyl]carbamic acid, ethyl ester A. N-(Ethoxycarbonyl)-2-nitroaniline To the solution of 2-nitroaniline (6.9 g, 50.0 mmol) in pyridine (6 mL) and dichloromethane (25 mL) at 0° C. under argon was added ethylchloroformate (7.3 mL, 75.0 mmol) through an addition funnel. After the addition was finished, the cooling bath was removed and the reaction mixture was allowed to stir at room temperature overnight. The reaction mixture was poured into 2N hydrochloric acid and extracted with ethyl acetate. The combined extracts were washed with water, saturated sodium bicarbonate solution and brine. After drying over anhydrous magnesium sulfate, the solvent was evaporated to yield the title compound as a yellow solid (7.7 g, 73.3%).

B. 2-[(Ethoxycarbonyl)amino]aniline

The solution of N-(ethoxycarbonyl)-2-nitroaniline (2.0 g, 9.5 mmol) in absolute ethanol (25 mL) was hydrogenated at atmospheric pressure in the presence of 10% palladium hydroxide/carbon catalyst (200 mg). The catalyst was filtered off using a celite pad and the filtrate was evaporated. The residue was crystallized from isopropyl ether to give 2-[(ethoxycarbonyl)amino]aniline as a colorless solid (820 mg, 64.6% ).

C. trans-[2-[(6-Cyano-3,4-dihydro-3-hydroxy-2,2-dimethyl-2H-pyran-4yl)aminolphenyl]carbamic acid, ethyl ester The reaction mixture containing compound of example 1, part B (900 mg, 5.0 mmol), 6-cyano-3,4-epoxy-3,4-dihydro-2,2-dimethyl-2H-benzopyran (prepared according to Evans et al., *J. Med. Chem.*, 1983, 26, 1582 and *J. Med Chem.*, 1986, 29, 2194) (1.0 g, 5.0 mmol) and magnesium perchlorate (1.12 g, 5.0 mmol) in acetonitrile (5.0 mL) was stirred under argon at room temperature for 48 hours. The reaction mixture was diluted with ethyl acetate and washed with water, saturated sodium bicarbonate solution and brine. After drying over anhydrous magnesium sulfate, the solvent was evaporated to give a colorless foam (2.02 g, 95.7%). This material was purified by flash chromatography (25% ethyl acetate in hexanes) to yield an amorphous solid, m.p. 138°-140° C. Microanalysis calculated for $C_{21}H_{23}N_3O_4 \cdot 0.3$ $Et_2O$: C,64.95; H,6.57; N,10.24. Found: C, 64.95; H,6.37; N,10.05.

EXAMPLE 2

(3S-trans)-[2-[(6-Cyano-3,4-dihydro-3-hydroxy-2,2-dimethyl-2H-pyran-4yl)amino]phenyl]carbamic acid, ethyl ester

A. (1αR-cis)-1a,7b-Dihydro-2,2-dimethyl-2H-oxireno-[c][1]benzopyran-6-carbonitrile A solution of 0.05M $Na_2HPO_4$ (10 mL) was added to a solution of undiluted commercial household bleach (25 mL). Sodium hydroxide (1N solution) was added dropwise to the resulting solution (0.55M in NaOCl) until pH≈11.3. This solution was cooled to 0° C. and then added to cold (0° C.) solution of Mn (III) salen complex (0.26 g, 0.4 mmol, described by N. H. Lee et al., *Tetrahedron Letters*, 1991, V. 32, p. 5055) and 6-cyano-2,2-dimethyl-2H-1-benzopyran (1.85 g, 10 mmol, prepared according to Evans et al., *J. Med. Chem.*, 1986, 29, p. 1582) in dichloromethane (10 mL). The two phase reaction mixture was stirred at 0° C. and monitored by TLC. After eight hours, the heterogeneous brown mixture was filtered through a pad of celite and the organic phase was separated. It was washed with brine (50 mL), dried over anhydrous magnesium sulfate and concentrated in vacuo to yield a fight yellow solid (2.0 g, 99%). The solid was recrystallized from aqueous ethanol to give the title A compound as a white solid (0.6 g), m.p. 128°-133° C.

$[\alpha_D]^{25} = +80.7°$ (c=1.166, MeOH). Analysis calculated for $C_{12}H_{11}N_2 \cdot 0.09$ $H_2O$: C,71.05; H,5.56; N,6.91. Found: C, 71.18; H,5.39; N, 6.78.

B. (3S-trans)-[2-[(6-Cyano-3,4-dihydro-3-hydroxy-2,2-dimethyl-2H-pyran-4yl)amino]phenyl]carbamic acid, ethyl ester The reaction mixture containing (1aS-cis)-1a,7b-dihydro-2,2-dimethyl-2H-oxireno-[c][1]benzopyran-6-carbonitrile, from example 2, part A (1.0 g, 5.0 mmol), 2-[(ethoxycarbonyl)amino]aniline, compound of example 1, part B (900 mg, 5.0 mmol) and magnesium perchlorate (1.12 g, 5.0 mmol) in acetonitrile (5.0 mL) was stirred under argon at room temperature for 48 hours. The reaction mixture was diluted with ethyl acetate and washed with water, saturated sodium bicarbonate solution and brine. After drying over anhydrous magnesium sulfate, the solvent was evaporated to give a colorless foam which was purified by flash chromatography (25% ethyl acetate in hexanes) to yield the title product as an amorphous solid (1.76 g, 92.8%) (shrinks at 84° C.). $[a]_D = +21°$ (c=1.1%, MeOH). Microanalysis calculated for $C_{21}H_{23}N_3O_4$: C,66.13; H, 6.08; N,11.02. Found: C, 66.11; H, 6.15; N, 10.78.

EXAMPLE 3

(3R-trans)-[2-[(6-Cyano-3,4-dihydro-3-hydroxy-2,2-dimethyl-2H-pyran-4yl)aminolphenyl]carbamic acid, ethyl ester The title compound was prepared from (1αR-cis)-1a,7b-dihydro-2,2-dimethyl-2H-oxireno-[c][1]benzopyran-6-carbonitrile and 2-[(ethoxycarbonyl)amino]aniline using the same procedure as described for (3S-trans)-[2-[(6-cyano-3,4-dihydro-3-hydroxy-2,2-dimethyl-2H-pyran-4yl)amino]phenyl]carbamic acid, ethyl ester (Example 3, part B). The product was obtained as an amorphous solid (shrinks at 84° C.). $[a]_D = -16°$ (c=1.1, MeOH). Microanalysis calculated for $C_{21}H_{23}N_3O_4$: C, 66.13; H, 6.08; N, 11.02. Found: C, 65.83; H, 6.14; N, 10.88.

EXAMPLE 4

(R)-1-(6-Cyano-3,4-dihydro-2,2-dimethyl-2H-benzopyran-4-yl)-1H-benzimidazole-2-carboxylic acid, ethyl ester

A. 6-Cyano-3.4-dihydro-2.2-dimethyl-2H-1-benzopyran

A solution of 6-cyano:2,2-dimethyl-2H-1-benzopyran (5.5 g, 29.7 mmoles, prepared according to Evans et al., *J. Med. Chem.*, 1983, 26, 1582 and *J. Med Chem,*, 1986, 29, 2194) in anhydrous ethanol (40 mL) was treated with 10% palladium over charcoal (0.35 g) and stirred under $H_2$ for two hours. The catalyst was filtered through Celite and the filter cake washed with ethyl acetate. The filtrate was concentrated under vacuum to obtain 5.71 g of a yellow oil. The crude product was dissolved in ethyl acetate (60 mL) and washed successively with 5% HCl solution (60 mL), saturated NaHCO$_3$ solution (60 mL), saturated NaCl solution (60 mL) and dried over MgSO$_4$. The solvent was recovered under vacuum to yield 5.14 g (92.4%) of the title compound as a yellow solid which crystallized on standing, m.p. 30°-31 ° C. Microanalysis calculated for $C_{12}H_{13}NO$: C,76.98; H, 7.00; N, 7.48. Found: C, 77.03; H, 7.02, N, 7.58.

B. 4-Bromo-6-cyano-3,4-dihydro-2,2-dimethyl-2H-1-benzopyran

To a solution of 6-cyano-3,4-dihydro-2,2-dimethyl-2H-1-benzopyran (6.40 g, 34.18 mmoles), title A compound, in carbon tetrachloride (90 mL) was added N-bromosuccinimide (6.69 g, 37.6 mmoles). The solution was purged with argon. A solution of Azobisisobutyronitrile (0.4 g, 3.42 mmoles) in carbon tetrachloride (10 mL) was added; the reaction was heated at reflux for 30 minutes with irradiation (high intensity visible light). The reaction mixture was concentrated under vacuum and the residue was dissolved in 75 mL ethyl acetate. The solution was washed successively with distilled water (4×75 mL), saturated sodium bicarbonate solution (75 mL), saturated NaCl solution (75 mL), and dried over magnesium sulfate. The solvent was recovered under vacuum to obtain an orange waxy solid which was triturated with cold pentane to provide a beige solid (7.19g). This was crystallized from ethyl acetate and hexanes (10:90) to yield the title compound (4.60 g) as off-white needles, m.p. 94°-95° C. The mother liquors were combined and chromatographed on silica gel eluting with hexane/ethyl acetate (19:1) to afford additional product (2.26 g) for a combined yield of 75.4%. Microanalysis calculated for $C_{12}H_{12}NOBr$: C, 54.16; H, 4.54; N, 5.26; Br, 30.02. Found: C, 54.55; H, 4.62; N, 5.46; Br, 29.86

C. 4-Azido-6-cyano-3,4-dihydro-2,2-dimethyl-2H-1-benzopyran

A solution of 4-bromo-6-cyano-3,4-dihydro-2,2-dimethyl-2H-1-benzopyran (6.73 g, 25.29 mmoles), title B compound, in dry N,N-dimethylformamide (100 mL) was treated with sodium azide (3.79 g, 50.57 mmoles) and stirred at room temperature under argon for 4 hours. The reaction mixture was partitioned between 100 mL ethyl acetate and 200 mL distilled water. The organic layer was separated and the aqueous layer was extracted with 100 mL of ethyl acetate. The combined organics were washed successively with distilled water, saturated sodium bicarbonate solution, brine and dried over magnesium sulfate. The solvent was evaporated under vacuum to obtain an orange gum (5.62 g) which was triturated with pentane to provide the title compound (4.50 g, 78%) as an off-white solid, m.p. 63°-64° C. Microanalysis calculated for $C_{12}H_{12}N_4O$: C, 63.15; H, 5.30; N, 24.55. Found: C, 63.57; H, 5.27; N, 24.75.

D. 4-Amino-6-cyano-3,4-(dihydro-2,2-dimethyl-2H-1-benzopyran

A solution of 4-azido-6-cyano-3,4-dihydro-2,2-dimethyl-2H-1-benzopyran (2.00 g, 8.77 mmol), title C compound, in absolute ethanol (50 mL) was treated with 10% palladium on charcoal (0.25 g) and stirred under hydrogen for 90 minutes at room temperature. The catalyst was filtered off and the filtrate was acidified to pH 1-2 with concentrated HCl (0.85 mL) and concentrated under vacuum to a white solid. The residue was dissolved in 100 mL distilled water and extracted with ethyl acetate (discarded). The aqueous layer was adjusted to pH 11-12 with 50% sodium hydroxide solution and extracted with ethyl acetate. The extracts were washed with brine and dried over magnesium sulfate. The solvent was evaporated under vacuum to provide the title compound (1.542 g, 87%) as a yellow oil which solidified upon standing. The product was used in the next step without further purification.

E. [4R (R*)]-N-(6-cyano-3,4-dihydro-2,2-dimethyl-2H-1-benzopyran-4-yl)-a-hydroxybenzeneacetamide and [4S(S*)]-N-(6-cyano-3,4-dihydro-2,2-dimethyl-2H-1-benzopyran-4-yl)-a-hydroxybenzeneacetamide To a solution of R-(-)-mandelic acid (22.1 g, 0.14 mole) and 1-hydroxybenzotriazole hydrate (19.6 g, 0.14 mole) cooled to 0° C. was added successively N-methylmorpholine (16.2 g, 0.16 mole), 4-amino-6-cyano-3,4-dihydro-2,2-dimethyl- 2H-1-benzopyran (29.4 g, 0.14 mole, title D compound) and 1-(3-dimethylaminopropyl)-2-ethylcarbodiimide hydrochloride (27.9 g, 0.14 mole). The reaction mixture was stirred 0.5 hours at 0° C. and two hours at room temperature. The solvent was recovered under vacuum and the residue was partitioned between 5% aqueous HCl and ethyl acetate. The organic fraction was washed with saturated sodium bicarbonate solution, saturated sodium chloride solution, dried over magnesium sulfate and evaporated in vacuo to obtain 52 g of a yellow gum. The crude diastereomeric mixture was chromatographed on silica eluting with 1:1 hexane/ethyl acetate to obtain [4R(R*)]-N-(6-cyano-3,4-dihydro-2,2-dimethyl-2H-1-benzopyran-4-yl)-α-hydroxybenzeneacetamide (23.2 g, 47.7%, m.p.=120°-121° C. $[a]^D{}_{25} = -39.5°$ (c=1.058, $CHCl_3$). From the column was also recovered [4S(S*)]-N-(6-cyano-3,4-dihydro-2,2-dimethyl-2H-1-benzopyran-4-yl)-α-hydroxybenzeneacetamide (19.8 g, 40.6%), m.p. 135°-136° C. $[a]^D{}_{25} = -60.8°$ (c=0.938, $CHCl_3$) )

F. (R)-4-amino-6-cyano-3,4-dihydroxy-2,2-dimethyl-2H-1-benzopyran and (S)-4-amino-6-cyano-3,4-dihydroxy-2,2-dimethyl-2H-1-benzopyran A solution of [4R(R*)]-N-(6-cyano-3,4-dihydro-2,2-dimethyl-2H-1-benzopyran-4-yl)-α-hydroxybenzeneacetamide, title E compound (22.3 g, 66.2) in a mixture of dioxane (195 mL) and 1.5M $H_2SO_4$ (140 mL) was heated at 75°-85° C. for five days. The reaction mixture was concentrated under vacuum and the concentrate was partitioned between distilled water and ethyl acetate. The aqueous phase was washed with ethyl acetate, made basic (pH>12) with 50% NaOH solution and extracted with diethyl ether. The ether extracts were washed with saturated NaCl solution, dried over $Na_2SO_4$ and evaporated in vacuo to obtain 9.58 g (72%) of the title compound as a yellow oil which crystallized on standing.

$[a]^D{}_{25} = -95.8°$ (c=0.976, $CHCl_3$).

Using the same procedure, (S)-4-amino-6-cyano-3,4-dihydroxy-2,2-dimethyl-2H-1-benzopyran was obtained from [4S(S*)]-N-(6-cyano-3,4-dihydro-2,2-dimethyl-2H-1-benzopyran-4-yl)-a-hydroxybenzeneacetamide (title E compound), as a colorless oil which solidified on standing. $[a]^D{}_{25} = +95.4°$ (c=0.982, $CHCl_3$).

G. (R)-4-[(2-Nitrophenyl)amino](6-cyano-3,4-dihydro-2,2-dimethyl-2H-1-benzopyran The reaction mixture containing (R)-4-amino-6-cyano-3,4-dihydro-2,2-dimethyl-2H-1-benzopyran (3.8 g, 18.8 mmol), the title F compound, 2-fluoronitrobenzene (2.6 mL, 24.5 mmol) and diisopropylethyl amine (4.9 mL, 28.2 mmol) in dimethylsulfoxide (10 mL) was heated at 100° C. for 16 hours. The yellow reaction mixture was cooled to room temperature and diluted with ether. The resulting solution was washed with water, 10% citric acid and brine. After drying over anhydrous magnesium sulfate, the solvent was evaporated and the residue was purified by flash chromatography (20% acetone in hexanes). The product was crystallized from ether-hexanes to yield the title compound (4.77 g, 78.6%) as a yellow solid, m.p. 125°–127° C. $[a]_D = -428°$ (c=0.5, MeOH). Microanalysis calculated for $C_{18}H_{17}N_3O_3$:C, 66.86; H, 5.30; N, 13.00. Found: C, 66.91; H, 5.28; N, 13.06.

H.
(R)-4-[(2-Aminophenyl)amino](6-cyano-3,4-dihydro-2,2-dimethyl-2H-1-benzopyran The suspension containing (R)-4-[(2-nitrophenyl)amino](6-cyano-3,4-dihydro-2,2-dimethyl-2H-1-benzopyran, title G compound (2.08 g, 6.43 mmol) in ethanol (20 mL) and conc. hydrochloric acid (10 mL) was cooled in ice bath and treated with granular tin metal (3.82 g, 32.2 mmol) in one portion. After 30 minutes, the cooling bath was removed and the reaction mixture was stirred vigorously at room temperature for five hours. The excess metal was removed and most of the solvent was evaporated under reduced pressure. The residue was diluted with dichloromethane (200 mL) and water (50 mL). It was cooled in an ice bath and treated with 6N sodium hydroxide until basic, pH approaching ≈11. The thick emulsion was filtered through a pad of celite and the organic layer was separated. The aqueous layer was reextracted with dichloromethane; combined organic extracts were dried over anhydrous potassium carbonate and the solvent was evaporated. The residue was crystallized from ether to give the title compound (1.51 g, 80%) as a colorless solid, m.p. 169°–171° C. Microanalysis calculated for $C_{18}H_{19}N_3O_{10}.25H_2O$: C, 72.57; H, 6.49; N, 14.11. Found: C, 72.65; H, 6.49; N, 14.03.

I.
[2-[(R)-(6-Cyano-3,4-dihydro-3-hydroxy-2,2-dimethyl-2H-pyran-4yl)amino]phenyl]oxamic acid, ethyl ester The solution of (R)-4-[(2-aminophenyl)amino](6-cyano-3,4-dihydro-2,2-dimethyl-2H-l-benzopyran, title H compound (1.15 g, 3.92 mmol) in dichloromethane (10 mL) and pyridine (1.2 mL) at 0° C. under argon was slowly treated with ethyloxalyl chloride (0.44 mL, 1.15 mmol). The reaction was stirred at 0° C. for 45 minutes and diluted with ethyl acetate. The resulting solution was washed with 10% citric acid, water, sodium bicarbonate and brine. It was dried over anhydrous magnesium sulfate and evaporated to yield a light yellow foam (1.7 g). This material was used for the next reaction without further purification.

J.
(R)-1-(6-Cyano-3,4-dihydro-2,2-dimethyl-2H-benzopyran-4-yl)- 1H-benzimidazole-2-carboxylic acid, ethyl ester The reaction mixture containing [2-[(R)-(6-cyano-3,4-dihydro-3-hydroxy-2,2-dimethyl-2H-pyran-4yl)amino]phenyl]oxamic acid, ethyl ester, title I compound (1.8 g, 4.58 retool) and phosphorus oxychloride (10 mL) was heated at 70° C. for five hours. It was cooled to room temperature and most of the phosphorus oxychloride was distilled off under vacuum. The residue in ethyl acetate was washed with 1N sodium hydroxide, brine, and was dried over anhydrous magnesium sulfate. The solvent was evaporated and the residue was purified by flash chromatography (5% ethyl acetate in dichloromethane) to yield the title compound as an off-white amorphous solid (1.08 g, 64.6%) (foams at 135° ). $[a]_D = +128.7°$ (c=0.66, MeOH). Microanalysis calculated for $C_{20}H_{16}N_3ClO_2$. 0.42 $H_2O$: C, 64.34; H, 4.54; N, 11.26. Found:,C, 64.68; H, 4.61; N, 10.82. Further elution of the column provided a light yellow foam (464 mg, 28.2%) which was crystallized from isopropyl ether to give (R)-4-[3-chloro-2-oxo-1(2H)-quinoxalinyl]-3,4-dihydro-2,2-dimethyl-2H-benzopyran-6-carbonitrile as colorless solid, m.p. 174°–176° C. $[a]_D = -90.2°$ (c=0.66, MeOH). Microanalysis calculated for $C_{22}H_{21}N_3O_2$* 1.1 $H_2O$: C, 69.66; H, 6.17; N, 11.08. Found: C, 69.85; H, 5.63; N, 10.89.

EXAMPLE 5
(S)-1-(6-Cyano-3,4-dihydro-2,2-dimethyl-2H-benzopyran-4-yl)-1H-benzimidazole-2-carboxylic acid, ethyl ester The title compound was prepared from (S)-4-amino-6-cyano-3,4-dihydro-2,2-dimethyl-2H-1-benzopyran (compound of title F, Example 4) by the same procedure as described for (R)-1-(6-cyano-3,4-dihydro-2,2-dimethyl-2H-benzopyran-4-yl)-1H-benzimidazole-2-carboxylic acid, ethyl ester in example 4, parts G–J. $[a]_D = -111°$ (c=0.5, MeOH). Microanalysis calculated for $C_{20}H_{16}N_3ClO_2.0.3\ H_2O$: C, 64.71; H, 4.51; N, 11.32, Cl, 9.55. Found: C, 65.08; H, 4.72; N, 10.76, Cl, 9.26. Further elution of the column also provided (R)-4-[3-Chloro-2-oxo-1(2H)-quinoxalinyl]-3,4-dihydro-2,2-dimethyl-2H-benzopyran-6-carbonitrile, m.p. 174°–175° C. $[a]_D = +92.1°$ (c=0.42, MeOH). Microanalysis calculated for $C_{22}H_{21}N_3O_2.0.7\ H_2O$: C, 68.10; H, 5.82; N, 10.83. Found: C, 68.07; H,5.55; N, 10.65.

What is claimed is;

1. A method for treating ischemia comprising administering to a mammalian specie in need thereof a therapeutically effective amount of a pharmaceutical composition comprising a compound of the formula

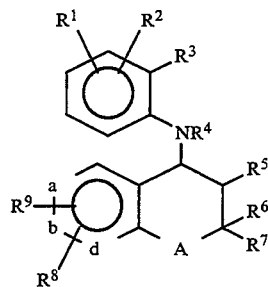

or pharmaceutically acceptable salts thereof wherein
a, b and d are all carbon atoms or one of a, b and d is a nitrogen atom or —N(O)— and the others are carbon atoms;

A is a single bond, —$CH_2$—, —O—, —S— or —N(-R)— where R is hydrogen, alkyl, haloalkyl, aryl, arylalkyl, cycloalkyl or (cycloalkyl)alkyl;

$R^1$ is hydrogen, alkyl, halo, haloalkyl, nitro or cyano:

$R^2$ is hydrogen, alkyl or halo;

$R^3$ is —COR, —CO-amino, —CO-substituted amino, —NRCOOR—*, —NRCO-amino or —NRCO-substituted amino (where R—* is the same or different R, as defined above);

$R^4$ is hydrogen, alkyl, alkenyl, aryl, aryl, alkyl, cycloalkyl or (cycloalkyl)alkyl; or $R^3$ and $R^4$ together with the carbon and nitrogen atoms to which they are attached, form a fused imidazole ring, unsubstituted or substituted at an available carbon atom of the imidazole portion with one or more substituents selected from hydrogen, alkyl, cyano, —COR, —COOR, —CO-amino, —CO-substituted amino, —NRCOOR—*, —NRCO-amino or —NRCO-substituted amino;

$R^5$ is hydrogen, hydroxy or —OC(O)R;

$R^6$ and $R^7$ are each independently hydrogen, alkyl or arylalkyl, or $R^6$ and $R^7$ taken together with the carbon atom to which they are attached form a 5- to 7-membered carbocyclic ring;

$R^8$ is hydrogen, alkyl, haloalkyl, alkenyl, alkynyl, cycloalkyl, arylalkyl, (cycloalkyl)alkyl, —CN, —$NO_2$, —COR, —COOR, —CONHR, —$CONR^5$, —$CF_3$, S-alkyl, —SOalkyl, —$SO_2$alkyl,

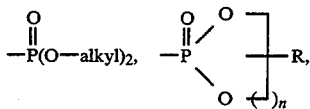

halogen, amino, substituted amino, —O-alkyl, —$OCF_3$, —$OCH_2CF_3$, —OCOalkyl, —OCONRalkyl, —NRCOalkyl, —NRCOOalkyl or-$NRCONR^5$;

$R^9$ is hydrogen, alkyl, hydroxy, —O—-alkyl, amino, substituted amino, —NHCOR, —CN or —$NO_2$; and n is an integer of 1 to 3; provided that when a, b and d are carbon atoms, $R^3$ is —NRCOOR*-and $R^4$ is hydrogen, that one of $R^1$ or $R^2$ is other than hydrogen; and a pharmaceutically acceptable carrier.

2. The method as recited in claim 1 wherein in the compounds of formula I;

$R^3$ and $R^4$ together with the carbon and nitrogen atoms to which they are attached, form a fused imidazole ring, unsubstituted or substituted at an available carbon atom of the imidazole portion with one or more substituents selected from hydrogen, alkyl, cyano, —COR, —COOR, —CO-amino, —CO-substituted amino, —NRCOOR*, —NRCO-amino or —NRCO-substituted amino.

3. The method as recited in claim 1 wherein in the compounds of formula I:

a, b and d are carbon atoms;

A is —O—;

$R^1$ and $R^2$ are hydrogens;

$R^3$ and $R^4$ together with the carbon and nitrogen atoms to which they are attached form a fused imidazole ring;

$R^5$ is hydrogen or hydroxy; and $R^6$ and $R^7$ are alkyl.

4. The method as recited in claim 1 wherein the compounds of formula I are:

(R)-1-(6-Cyano-3,4-dihydro-2,2-dimethyl-2H-benzopyran-4-yl)-1H-benzimidazole-2-carboxylic acid, ethyl ester, or (S)-1-(6-Cyano-3,4-dihydro-2,2-dimethyl-2H-benzopyran-4-yl)-1H-benzimidazole-2-carboxylic acid, ethyl ester, or a pharmaceutically acceptable salt thereof.

* * * * *